(12) United States Patent
Ahmad

(10) Patent No.: US 7,662,157 B2
(45) Date of Patent: Feb. 16, 2010

(54) BONE ANCHOR SYSTEM

(75) Inventor: Shaher A. Ahmad, Plano, TX (US)

(73) Assignee: OsteoMed L.P., Addison, TX (US)

( * ) Notice: Subject to any disclaimer, the term of this patent is extended or adjusted under 35 U.S.C. 154(b) by 722 days.

(21) Appl. No.: 10/645,739

(22) Filed: Aug. 21, 2003

(65) Prior Publication Data

US 2005/0043735 A1 Feb. 24, 2005

(51) Int. Cl.
*A61B 17/60* (2006.01)
(52) U.S. Cl. .................... 606/104; 606/86 A; 606/300; 606/916
(58) Field of Classification Search .......... 606/72, 606/73, 96, 104, 232, 99, 86 A, 916, 300–321; 623/13.14; 411/24; 81/52, 436, 58.1; 29/255, 29/278; 7/165; D8/83; 600/414, 424, 426; 433/174
See application file for complete search history.

(56) References Cited

U.S. PATENT DOCUMENTS

| | | | | |
|---|---|---|---|---|
| 3,508,455 A | * | 4/1970 | Miller | 81/58.1 |
| 4,713,004 A | * | 12/1987 | Linkow et al. | 433/174 |
| 4,938,768 A | | 7/1990 | Wu | |
| 4,945,914 A | | 8/1990 | Allen | |
| 4,991,579 A | | 2/1991 | Allen | |
| 5,061,181 A | * | 10/1991 | Niznick | 433/174 |
| 5,094,241 A | | 3/1992 | Allen | |
| 5,119,817 A | | 6/1992 | Allen | |
| 5,142,930 A | | 9/1992 | Allen et al. | |
| 5,178,164 A | | 1/1993 | Allen | |
| 5,209,659 A | * | 5/1993 | Friedman et al. | 433/173 |
| 5,222,499 A | | 6/1993 | Allen et al. | |
| 5,230,338 A | | 7/1993 | Allen et al. | |
| 5,282,746 A | * | 2/1994 | Sellers et al. | 433/172 |
| 5,299,253 A | | 3/1994 | Wessels | |

(Continued)

FOREIGN PATENT DOCUMENTS

EP 0 705 574 A2 4/1996

(Continued)

OTHER PUBLICATIONS

Z-Kat, *Acustar®*, Website system overview, 1 page, 1997-2002.

(Continued)

*Primary Examiner*—Thomas C Barrett
*Assistant Examiner*—James L. Swiger
(74) *Attorney, Agent, or Firm*—Baker Botts L.L.P.

(57) ABSTRACT

A bone anchor includes a screw portion configured to penetrate a bone. The screw portion includes a retention thread extending at least part of a length of the screw portion and a tip at a first end of the screw portion. The bone anchor includes a protrusion adjacent a second end of the screw portion. The second end is opposite the first end of the screw portion. The protrusion comprises a plurality of external sides forming a shape and a rounded interior surface enclosing a protrusion recess. The rounded interior surface includes a recess thread configured to retain a component at least partially in the protrusion recess. The protrusion has a maximum width that is less than a maximum diameter of the screw portion such that a shoulder is formed where the protrusion meets the second end of the screw portion.

8 Claims, 2 Drawing Sheets

U.S. PATENT DOCUMENTS

| | | | |
|---|---|---|---|
| 5,338,197 A * | 8/1994 | Kwan | 433/174 |
| 5,394,457 A | 2/1995 | Leibinger et al. | |
| 5,394,875 A | 3/1995 | Lewis et al. | |
| 5,397,329 A | 3/1995 | Allen | |
| 5,417,692 A * | 5/1995 | Goble et al. | 606/73 |
| 5,551,429 A | 9/1996 | Fitzpatrick et al. | |
| 5,566,081 A | 10/1996 | Yoshizawa et al. | |
| 5,575,794 A | 11/1996 | Walus et al. | |
| 5,590,215 A | 12/1996 | Allen | |
| 5,595,193 A | 1/1997 | Walus et al. | |
| 5,601,429 A | 2/1997 | Blacklock | |
| 5,643,320 A | 7/1997 | Lower et al. | |
| 5,662,683 A * | 9/1997 | Kay | 606/232 |
| 5,730,130 A | 3/1998 | Fitzpatrick et al. | |
| 5,743,899 A | 4/1998 | Zinreich | |
| 5,769,789 A | 6/1998 | Wang et al. | |
| 5,799,099 A | 8/1998 | Wang et al. | |
| 5,842,865 A * | 12/1998 | Bassett et al. | 433/174 |
| 5,897,319 A * | 4/1999 | Wagner et al. | 433/174 |
| 5,916,164 A | 6/1999 | Fitzpatrick et al. | |
| 5,984,930 A | 11/1999 | Maciunas et al. | |
| 5,989,028 A * | 11/1999 | Niznick | 433/173 |
| 6,052,477 A | 4/2000 | Wang et al. | |
| 6,073,044 A | 6/2000 | Fitzpatrick et al. | |
| 6,096,048 A | 8/2000 | Howard, III et al. | |
| 6,139,565 A | 10/2000 | Stone et al. | |
| 6,187,018 B1 | 2/2001 | Sanjay-Gopal et al. | |
| 6,226,548 B1 * | 5/2001 | Foley et al. | 600/426 |
| 6,258,091 B1 | 7/2001 | Sevrain et al. | |
| 6,298,262 B1 | 10/2001 | Franck et al. | |
| 6,327,491 B1 | 12/2001 | Franklin et al. | |
| 6,333,971 B2 * | 12/2001 | McCrory et al. | 378/162 |
| 6,413,260 B1 * | 7/2002 | Berrevoets et al. | 606/73 |
| 6,997,711 B2 * | 2/2006 | Miller | 433/174 |
| 2001/0004395 A1 | 6/2001 | McCrory et al. | |
| 2004/0030237 A1 * | 2/2004 | Lee et al. | 600/414 |
| 2004/0231468 A1 * | 11/2004 | Odachowski | 81/58.1 |

FOREIGN PATENT DOCUMENTS

| | | |
|---|---|---|
| WO | WO 99/39653 | 8/1999 |

OTHER PUBLICATIONS

Clarysse, et al., *A Computer-Assisted System for 3-D Frameless Localization in Stereotaxic MRI*, IEEE Transactions on Medical Imaging, vol. 10, pp. 523-529, Dec. 1991.

Rousseau, et al., "*Validation of a New Method for Stereotactic Localization Using MR Imaging*", Journal of Computer Assisted Tomography, vol. 15, No. 2, pp. 291-296, 1991.

Rousseau, et al., "*A Frameless Method for 3D MRI- and CT-Guided Stereotaxic Localisation*", European Radiology, vol. 2, No. 1, Cover, 3 table of contents pages, and article pp. 35-41, 1992.

PCT, Invitation to Pay Additional Fees, Annex to Form PCT/ISA/206 Communication Relating to the Results of the Partial International Search dated Jan. 10, 2005 for International Application No. PCT/US2004/027010, 9 pages, Jan. 10, 2005.

* cited by examiner

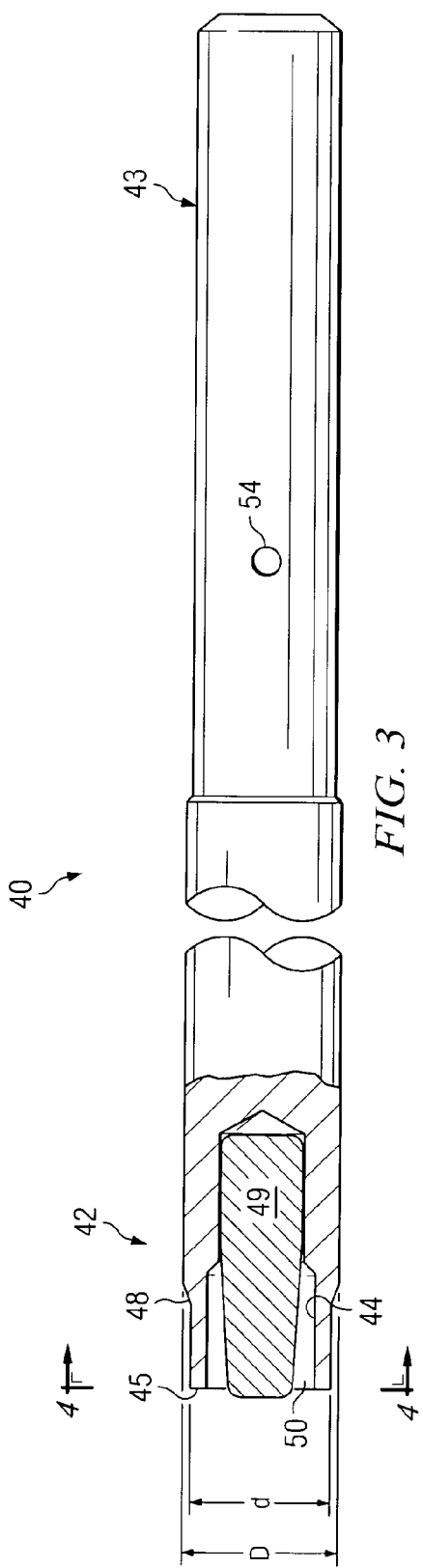
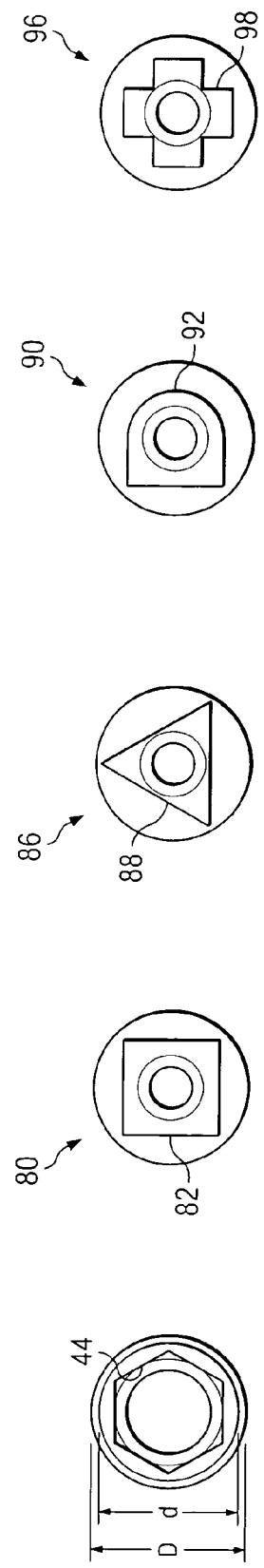

BONE ANCHOR SYSTEM

TECHNICAL FIELD OF THE INVENTION

This invention relates in general to medical devices and, more particularly, to a bone anchor system.

BACKGROUND OF THE INVENTION

In various surgical procedures, it is necessary to implant an anchor device in a bone for the installation and use of medical components. For example, an anchor device may be inserted into a bone to aid in the use of fiducial marker components, such as navigation landmarks in frameless stereotactic neurosurgical procedures. Such procedures may include tumor resections, deep brain stimulations, neuro-endoscopy and other deep brain access procedures. Some fiducial marker components may be screwed into the anchor device. In some cases, a separate device may be needed to hold the medical components in place. Moreover, when the anchor device is fully inserted into a bone using an installation tool, part of the device may extend beyond the surface of the bone.

SUMMARY OF THE INVENTION

The present invention provides a bone anchor system that substantially eliminates or reduces at least some of the disadvantages and problems associated with previous medical devices.

In accordance with a particular embodiment of the present invention, a bone anchor includes a screw portion configured to penetrate a bone. The screw portion includes a retention thread extending at least part of a length of the screw portion and a tip at a first end of the screw portion. The bone anchor includes a protrusion adjacent a second end of the screw portion. The second end is opposite the first end of the screw portion. The protrusion comprises a plurality of external sides forming a shape and a rounded interior surface enclosing a protrusion recess. The rounded interior surface includes a recess thread configured to retain a component at least partially in the protrusion recess. The protrusion has a maximum width that is less than a maximum diameter of the screw portion such that a shoulder is formed where the protrusion meets the second end of the screw portion.

The screw portion may comprise a conical shape and at least one cutting flute extending at least part of the length of the screw portion through the retention thread. The shape may comprise a hexagonal shape, a cruciform shape or an approximate D-shape. The bone anchor may comprise a length of approximately 0.20 inch. The component may comprise a fiducial marker component.

In accordance with another embodiment, a system for inserting a bone anchor into a bone includes a bone anchor comprising a screw portion configured to penetrate a bone. The screw portion comprises a retention thread extending at least part of a length of the screw portion and a tip at a first end of the screw portion. The bone anchor comprises a protrusion adjacent a second end of the screw portion. The second end is opposite the first end of the screw portion. The protrusion comprises a plurality of external sides forming a shape and a rounded interior surface enclosing a protrusion recess. The rounded interior surface includes a recess thread configured to retain a component at least partially in the protrusion recess when inserted into the bone. The protrusion has a maximum width that is less than a maximum diameter of the screw portion such that a shoulder is formed where the protrusion meets the second end of the screw portion. The system also includes a driver comprising a tip portion having a first diameter. The tip portion comprises a driver edge, an external surface and a plurality of internal surfaces enclosing a driver recess. The plurality of internal surfaces form the shape. The driver also comprises a second portion adjacent the tip portion and having a second diameter that is greater than the first diameter such that a rim is formed where the tip portion meets the second portion. The tip portion positions around the protrusion when the driver is used to insert the bone anchor into the bone. The driver edge contacts the shoulder during insertion. A distance between the driver edge and the rim of the driver is approximately equal to a distance between the shoulder and an end of the protrusion of the bone anchor such that when the rim contacts a surface of the bone during insertion the end of the protrusion will be approximately level with the surface of the bone.

Technical advantages of particular embodiments of the present invention include a self-drilling, self-tapping bone anchor with a threaded protrusion recess to allow various surgical components to be secured within the anchor. The components may include fiducial marker components. Thus, the need for additional devices to hold the surgical components in place during operation is reduced.

Another technical advantage of particular embodiments of the present invention includes a bone anchor insertion system with a driver that is configured to insert the anchor into a bone. The driver and the bone anchor may be frictionally coupled together. The driver and bone anchor may be configured such that after the bone anchor is fully inserted into the bone using the driver and the driver is uncoupled from the anchor, the anchor is flush-mounted within the bone. Accordingly, no part of the bone anchor extends beyond the bone's surface when the anchor is fully installed.

Other technical advantages will be readily apparent to one skilled in the art from the following figures, descriptions and claims. Moreover, while specific advantages have been enumerated above, various embodiments may include all, some or none of the enumerated advantages.

BRIEF DESCRIPTION OF THE DRAWINGS

For a more complete understanding of particular embodiments of the invention and their advantages, reference is now made to the following descriptions, taken in conjunction with the accompanying drawings, in which:

FIG. 3 illustrates a driver used to insert the bone anchor of FIGS. 1 and 2 into a bone, in accordance with a particular embodiment of the present invention;

FIG. 4 is a side view of the driver of FIG. 3 taken along line 4-4 of FIG. 3;

FIG. 5 is a side view of a bone anchor having a protrusion with a square configuration, in accordance with another embodiment of the present invention;

FIG. 6 is a side view of a bone anchor having a protrusion with a triangular configuration, in accordance with another embodiment of the present invention;

FIG. 7 is a side view of a bone anchor having a protrusion with an approximate D-shaped configuration, in accordance with another embodiment of the present invention; and FIG. 8 is a side view of a bone anchor having a protrusion with a cruciform configuration, in accordance with another embodiment of the present invention.

DETAILED DESCRIPTION OF THE INVENTION

Figure 1:
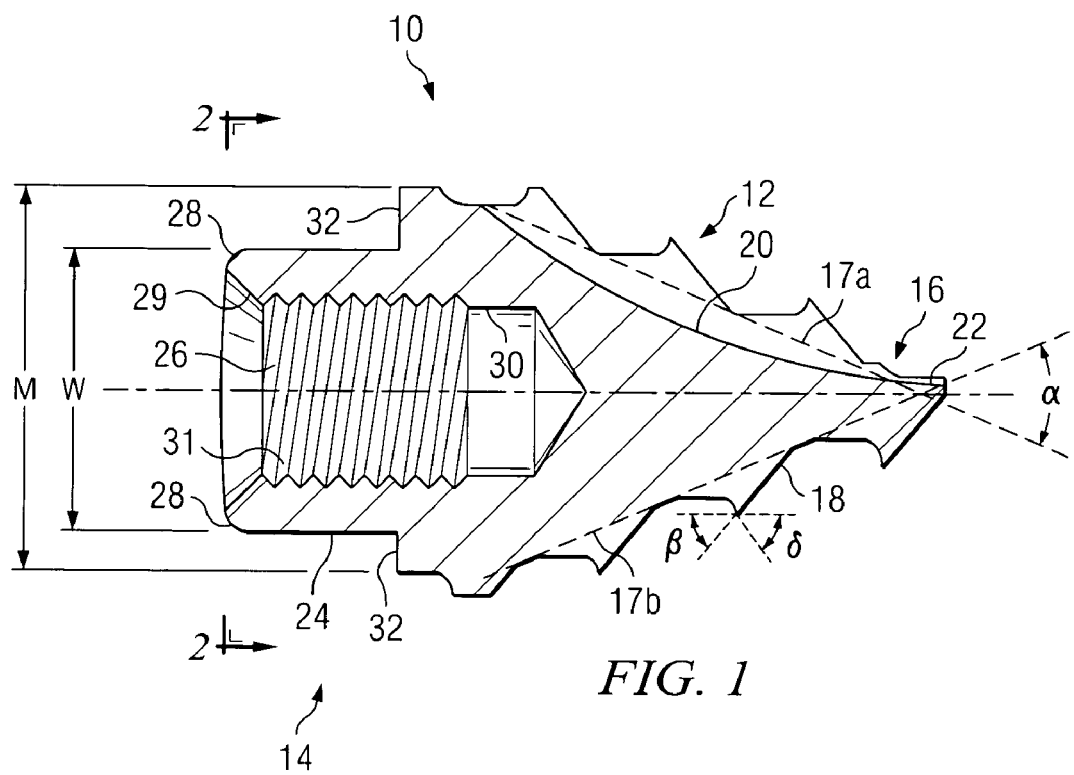
FIG. 1 illustrates a cross-sectional view of a bone anchor, in accordance with a particular embodiment of the present invention.

FIG. 1 illustrates a bone anchor 10, in accordance with a particular embodiment of the present invention. Bone anchor 10 is used to anchor, in a skull or other type of bone, accessories used in medical procedures involving the bone. In particular embodiments, bone anchor 10 may anchor accessories designed to establish fiducial markers, such as navigation landmarks in frameless stereotactic neurosurgical procedures. Such procedures may include tumor resections, deep brain stimulations, neuro-endoscopy and other deep brain access procedures. The accessories may be positioned in a recess partially enclosed by bone anchor 10 when anchor 10 is anchored in the bone. Bone anchor 10 includes an internal thread for securing accessories or other components within a recess of the anchor after insertion. Moreover, when inserted in a bone using a driver as discussed herein, bone anchor 10 may be flush-mounted in the bone such that its outermost end is approximately level with the bone's surface.

In the illustrated embodiment, bone anchor 10 includes a self-drilling, self-tapping screw region 12 and a head region 14. Because screw region 12 is self-drilling and self-tapping, it may be installed without the need to pre-drill an aperture to receive it and without the need to pre-tap threads in a hole formed in the bone. These characteristics also provide increased surface contact between the bone and screw region retention thread thus improving the holding power of the screw region. Bone anchors that require pre-drilling and/or pre-tapping may be used within the teachings of the present invention.

In this embodiment, screw region 12 includes a conically-shaped portion with a tip 22 at one of its ends for penetrating the skull to initiate drilling. Other embodiments may include a screw region having other configurations, such as a cylindrically-shaped portion adjacent a conically-shaped portion with a tip. Screw region 12 includes a retention thread 18 that extends substantially through its length. One end of retention thread 18 is very near tip 22 thus aiding in the self-tapping characteristics of screw region 12. Particular embodiments may include more than one retention thread. In some embodiments, retention thread 18 may have a lead angle β between approximately 48° and 52° (for example 50°) and a trailing angle δ between approximately 78° and 82° (for example 80°), each such angle as measured from a center line of bone anchor 10. In some embodiments, both the lead and trail angles and the pitch of retention thread 18 may change across the length of screw region 12.

Bone anchor 10 has an included angle α proximate tip 22. As illustrated, included angle α is defined by the angle between two imaginary lines 17a and 17b that each connect tangent points of an inside radii of retention thread 18. In this embodiment, included angle α is approximately 46°. In particular embodiments this included angle α may vary from approximately 46° to 49° to provide a desirable combination of both penetrability and strength.

Screw region 12 includes a cutting flute 20 extending over at least some portion of the length of screw region 12. Cutting flute 20 is a cutting surface which will engage the bone as the screw region is rotated in a clockwise direction into the bone. In this embodiment, cutting flute 20 extends through screw region 12 to tip 22. Cutting flute 20 cuts and removes bone fragments from the skull or other bone in which bone anchor 10 is being inserted in order to permit threads to be formed therein. Thus, cutting flute 20 provides self-tapping characteristics to screw region 12. Cutting flute 20 may be formed by plunging a mill (not illustrated) proximate tip 22 and removing material towards a center line of screw region 12. The configuration of screw region 12 proximate tip 22, including included angle α and retention thread 18 extending to tip 22, and the position of cutting flute 20 result in minimal amount of bone material being removed prior to thread engagement. This helps to maximize the amount of bone in contact with bone anchor 10 during insertion and when anchored. Particular embodiments may include more than one cutting flute. For example, some embodiments may include two cutting flutes 180° apart.

The overall length of bone anchor 10 may be different in various embodiments; however, in particular embodiments such overall length may be approximately 0.12 to 0.24 inch, for example 0.20 inch. Bone anchor 10 may be composed of any suitable medical grade, biocompatible material. Examples of such material may include titanium, a titanium alloy, cobalt chrome, a high strength resinous polymer, implantable grade stainless steel, bioresorbable polymer or other material. This choice of material helps to provide the strength required to withstand the drive torque bone anchor 10 will experience during insertion into the bone.

Head region 14 is proximate an end of screw region 12 opposite from tip 22. Head region 14 includes a protrusion 24 having a recess 26 extending therethrough and into screw region 12. In this embodiment, protrusion 24 has a hexagonal configuration as evident with respect to FIG. 2 discussed below; however, head regions of bone anchors in accordance with other embodiments may include a protrusion having other configurations. The hexagonal configuration of protrusion 24 helps to maximize the torque that can be delivered to bone anchor 10 during insertion. Top edge 28 of protrusion 24 may have a rounded configuration for less obtrusiveness.

Protrusion 24 includes rounded interior surface 30 surrounding recess 26. A chamfered interior surface 29 may exist at the entrance to recess 26. Interior surface 30 is threaded with thread 31 for receiving accessories or other components when bone anchor 10 is installed in a skull. Such accessories may include a fiducial marker component. Thread 31 of interior surface 30 may extend partially or substantially through the length of interior surface 30. Other embodiments may include more than one thread 31. Since a maximum width W of protrusion 24 is less than the diameter of the end of screw region 12 from which protrusion 24 extends, then a shoulder 32, having a diameter M, is formed at such end. In particular embodiments, width W may be approximately 0.077 inch.

Figure 2:
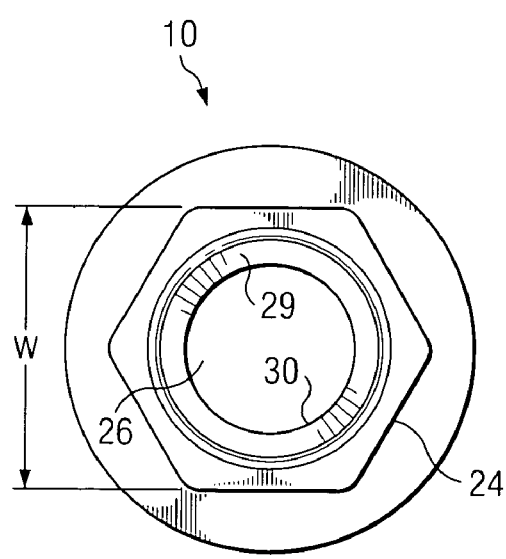
FIG. 2 is a side view of the bone anchor of FIG. 1, taken along line 2-2 of FIG. 1.

FIG. 2 is a side view of bone anchor 10 of FIG. 1 taken along line 2-2 of FIG. 1. As discussed above, protrusion 24 has a hexagonal configuration.

FIGS. 3 and 4 illustrate a driver 40, used to insert bone anchor 10 into a bone, in accordance with a particular embodiment of the present invention. FIG. 4 is a cross-sectional view of driver 40 of FIG. 3 taken along line 4-4 of FIG. 3. Driver 40 includes a tip portion 42 at its end that contacts the bone anchor during insertion. Tip portion 42 includes an edge 45 at such end of driver 40. Tip portion 42 includes inside edges 44 which, in this embodiment, form a hex socket as illustrated in FIG. 4 to provide a close fit with a bone anchor having a protrusion with a similar hexagonal configuration (such as bone anchor 10 of FIGS. 1 and 2) for maximization of torque delivered to the anchor. Drivers of other embodiments may include a tip portion with inside edges forming a different configuration that may match a similar configuration of a bone anchor protrusion. Tip portion 42 has a diameter d slightly smaller than a diameter D of the portion of driver 40 adjacent tip portion 42. Such change in diameter forms a rim 48 encircling driver 40.

Disposed within driver 40 proximate end 45 is an insert 49 comprising a rubber-like material. In particular embodiments, insert 49 may comprise silicon. When inserting bone anchor 10 into a skull or other bone using driver 40, bone anchor 10 is positioned such that its protrusion 24 is inside gap 50 formed between inside edges 44 and insert 49. Insert 49 is positioned at least partially within recess 26 of anchor 10. The rubber-like material of insert 49 helps to form a friction fit with thread 31 of interior surface 30 so that anchor 10 does not easily separate from driver 40 during insertion into a bone.

During insertion of the bone anchor, edge 45 of tip portion 42 contacts shoulder 32 of bone anchor 10. Diameter d of tip portion 42 is approximately equal to diameter M of bone anchor 10 at shoulder 32. Thus, when bone anchor 10 is inserted in a bone using driver 40, tip portion 42 of driver 40 enters the hole in the bone formed by screw region 12 until rim 48 (having a larger diameter D than diameter d of tip portion 42) contacts the surface of the bone. Driver 40 is then withdrawn from the bone as retention thread 18 secures bone anchor 10 in place within the bone. Thus, top edge 28 of protrusion 24 of bone anchor 10 is approximately level with the surface of the bone such that bone anchor 10 is flush mounted within the bone.

The length of protrusion 24 from its edge 28 to shoulder 32 may be different in various embodiments; however, in particular embodiments such length may be approximately 0.05 inches. In some embodiments, such length of protrusion 24 may be altered relative to the length of tip portion 42 of driver 40 such that bone anchor 10 may not be flush mounted within the skull when inserted. For example, if the length of protrusion 24 was greater than the length of tip portion 42 then protrusion 24 would extend partially out of the skull when inserted using the driver, because rim 48 would contact the surface of the skull before top edge 28 of protrusion 24 had reached the level of the skull surface. Likewise, if protrusion 24 had a length less than the length of tip portion 42 then when completely inserted using driver 40, bone anchor 10 would rest entirely below the surface of the skull.

One or more detents 54 provide a manner to engage the rounded surfaces of handle portion 43 and to provide torque during use of driver 40. In particular embodiments, a grip handle may be cast over handle portion 43 for insertion of the bone anchor. The grip handle may include a plurality of grooves longitudinally disposed on the exterior of the handle to provide a surface for a surgeon to grip. Other gripping features may also be used in lieu of or in addition to the longitudinal grooves. For example, knurled surfaces and/or other indentations may be provided. Moreover, driver 40 may be configured to cooperate with a power instrument to rotate the driver for insertion of the bone anchor. Such a power instrument may include a torque limiting device. Furthermore, a grip portion of the driver may be constructed of a number of surgical grade materials, such as metal, plastic, alloys or a combination thereof.

FIGS. 5-8 illustrate cross-sections of bone anchors, in accordance with other embodiments of the present invention. In FIG. 5, a protrusion 82 of a bone anchor 80 has a square configuration. In FIG. 6, a protrusion 88 of a bone anchor 86 has a triangular configuration. In FIG. 7, a protrusion 92 of a bone anchor 90 has an approximate D-shaped configuration. In FIG. 8, a protrusion 98 of a bone anchor 96 has a cruciform configuration. As indicated above, protrusions of bone anchors in other embodiments may include other configurations or shapes. As is the case with driver 40 and bone anchor 10 discussed above, drivers used to insert such bone anchors may include inside edges at their tip regions that form configurations that match the configurations of the particular bone anchors being inserted by the drivers.

Although the present invention has been described in detail, various changes and modifications may be suggested to one skilled in the art. It is intended that the present invention encompass such changes and modifications as falling within the scope of the appended claims.

What is claimed is:

1. A driver for inserting a bone anchor into a bone, comprising:
   a tip portion having a first diameter, the tip portion comprising:
      a driver edge;
      an external surface; and
      a plurality of internal surfaces enclosing a driver recess, wherein the plurality of internal surfaces form a shape;
      an insert retained in the driver recess and configured to be positioned at least partially within a threaded protrusion recess of a protrusion of the bone anchor to provide a friction fit between the driver and the bone anchor during insertion of the bone anchor;
   a second portion adjacent the tip portion, the second portion having a second diameter, the second diameter greater than a first diameter such that a rim is formed where the tip portion meets the second portion; and
   wherein the tip portion is configured to be positioned around the protrusion of the bone anchor when the driver is used to insert the bone anchor into a bone, the driver edge configured to contact a shoulder of the bone anchor during insertion.

2. The driver of claim 1, wherein the insert comprises silicon.

3. The driver of claim 1, wherein the shape comprises a hexagonal shape.

4. The driver of claim 1, wherein the first diameter is approximately equal to a shoulder diameter of the shoulder of the bone anchor.

5. The driver of claim 1, wherein a distance between the driver edge and the rim is approximately equal to a distance between the shoulder of the bone anchor and an end of the protrusion.

6. A driver for inserting a bone anchor into a bone, comprising:
   a tip portion having a first diameter, the tip portion comprising:
      a driver edge;
      an external surface; and
      a plurality of internal surfaces enclosing a driver recess, wherein the plurality of internal surfaces form a shape;
   an insert retained in the driver recess and configured to be positioned at least partially within a threaded protrusion recess of a protrusion of the bone anchor to provide a friction fit between the driver and the bone anchor during insertion of the bone anchor;
   a second portion adjacent the tip portion, the second portion having a second diameter, the second diameter greater than a first diameter such that a rim is formed where the tip portion meets the second portion;
   wherein the tip portion is configured to be positioned around the protrusion of the bone anchor when the driver is used to insert the bone anchor into a bone, the driver edge configured to contact a shoulder of the bone anchor during insertion; and
   wherein a distance between the driver edge and the rim is approximately equal to a distance between the shoulder of the bone anchor and an end of the protrusion.

7. A driver for inserting a bone anchor into a bone, comprising:
a tip portion having a first diameter, the tip portion comprising:
a driver edge;
an external surface; and
a plurality of internal surfaces enclosing a driver recess, wherein the plurality of internal surfaces form a hexagonal shape;
a silicon insert retained in the driver recess and positioned at least partially within a threaded protrusion recess of a protrusion of the bone anchor to provide a friction fit between the driver and the bone anchor during insertion of the bone anchor;
a second portion adjacent the tip portion, the second portion having a second diameter, the second diameter greater than the first diameter such that a rim is formed where the tip portion meets the second portion;
wherein the tip portion positions around a protrusion of a bone anchor when the driver is used to insert the bone anchor into a bone, the driver edge contacting a shoulder of the bone anchor during insertion;
wherein the first diameter is approximately equal to a shoulder diameter of the shoulder of the bone anchor; and
wherein a distance between the driver edge and the rim is approximately equal to a distance between the shoulder of the bone anchor and an end of the protrusion.

8. A bone anchor, comprising:
a screw portion having a conical shape and being configured to penetrate a bone, the screw portion comprising:
a retention thread extending at least part of a length of the screw portion; and
a tip at a first end of the screw portion;
a first and a second cutting flute approximately 180° apart, each cutting flute extending at least part of a length of the screw portion through the retention thread; and
wherein the retention thread comprises a lead angle approximately equal to 50° and a trailing angle approximately equal to 80°, the lead and the trailing angle each being measured from a longitudinal axis of the screw portion;
a protrusion adjacent a second end of the screw portion, the second end opposite the first end of the screw portion, the protrusion comprising:
a plurality of external sides forming a hexagonal shape;
a rounded interior surface enclosing a protrusion recess, the rounded interior surface including a single, continuous recess thread extending a majority of a length of the protrusion recess, the recess thread being configured to rotatably retain a threaded fiducial marker component at least partially in the protrusion recess;
a top surface having a rounded edge;
wherein the protrusion has a maximum width approximately equal to 0.077 inch, the maximum width being less than a maximum diameter of the screw portion such that a shoulder is formed where the protrusion meets the second end of the screw portion;
wherein the shoulder further comprises a continuous shoulder surface extending around the protrusion, the entire shoulder surface being oriented generally perpendicular to the longitudinal axis of the screw portion; and
wherein the protrusion recess has an entrance comprising a chamfered interior surface; and
wherein the bone anchor has a length of approximately 0.20 inch.

* * * * *

UNITED STATES PATENT AND TRADEMARK OFFICE
CERTIFICATE OF CORRECTION

PATENT NO. : 7,662,157 B2  Page 1 of 1
APPLICATION NO. : 10/645739
DATED : February 16, 2010
INVENTOR(S) : Shaher A. Ahmad It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1032 days.

Signed and Sealed this

Thirtieth Day of November, 2010

David J. Kappos
*Director of the United States Patent and Trademark Office*